US012564418B2

(12) United States Patent
    Cowley et al.

(10) Patent No.:     US 12,564,418 B2
(45) Date of Patent:        Mar. 3, 2026

(54) ARTICULATING ULTRASONIC SURGICAL INSTRUMENTS AND SYSTEMS

(71) Applicant: Covidien LP, Mansfield, MA (US)

(72) Inventors: Matthew S. Cowley, Frederick, CO (US); Thomas E. Drochner, Longmont, CO (US); David J. Van Tol, Boulder, CO (US); Michael B. Lyons, Boulder, CO (US); James R. Fagan, Erie, CO (US)

(73) Assignee: Covidien LP, Mansfield, MA (US)

( * ) Notice: Subject to any disclaimer, the term of this patent is extended or adjusted under 35 U.S.C. 154(b) by 392 days.

(21) Appl. No.: 17/924,596

(22) PCT Filed: May 3, 2021

(86) PCT No.: PCT/US2021/030438
    § 371 (c)(1),
    (2) Date: Nov. 10, 2022

(87) PCT Pub. No.: WO2021/231118
    PCT Pub. Date: Nov. 18, 2021

(65) Prior Publication Data
    US 2023/0172628 A1      Jun. 8, 2023
    Related U.S. Application Data

(60) Provisional application No. 63/025,337, filed on May 15, 2020.

(51) Int. Cl.
    *A61B 17/32*        (2006.01)
    *A61B 17/22*        (2006.01)
    *A61B 34/30*        (2016.01)
(52) U.S. Cl.
    CPC .. *A61B 17/320092* (2013.01); *A61B 17/2202* (2013.01); *A61B 2017/320089* (2017.08);
    (Continued)

(58) Field of Classification Search
    CPC ........ A61B 17/320092; A61B 17/2202; A61B 2017/320089; A61B 2017/320093;
    (Continued)

(56) References Cited

U.S. PATENT DOCUMENTS

| | | | |
|---|---|---|---|
| 5,792,135 A | 8/1998 | Madhani et al. | |
| 5,897,523 A | 4/1999 | Wright et al. | |

(Continued)

FOREIGN PATENT DOCUMENTS

| | | | |
|---|---|---|---|
| JP | 2001000444 A | * | 1/2001 |
| WO | 2009018409 A2 | | 2/2009 |

(Continued)

OTHER PUBLICATIONS

Espacenet translation of JP 2001000444 A (Year: 2001).*

(Continued)

*Primary Examiner* — Darwin P Erezo
*Assistant Examiner* — Zehra Jaffri

(57)        ABSTRACT

An ultrasonic surgical instrument includes a housing, an elongated shaft extending distally from the housing, an end effector extending distally from the elongated shaft, and a transducer assembly disposed at least partially within the elongated shaft. The end effector includes a jaw and an ultrasonic blade. The jaw is configured to pivot relative to the ultrasonic blade from an open position to a clamping position for clamping tissue therebetween. The transducer assembly is distally-spaced from the housing and includes proximal and distal transducers interconnected by a connector. The ultrasonic blade is connected to the distal transducer such that ultrasonic energy produced by the proximal transducer is transmitted along the connector and the distal transducer to the ultrasonic blade and such that ultrasonic energy produced by the distal transducer is transmitted to the ultrasonic blade.

18 Claims, 5 Drawing Sheets

(52) U.S. Cl.
CPC ............. *A61B 2017/320093* (2017.08); *A61B 2017/320094* (2017.08); *A61B 2034/305* (2016.02)

(58) Field of Classification Search
CPC .. A61B 2017/320094; A61B 2034/305; A61B 2017/320071
See application file for complete search history.

(56) References Cited

U.S. PATENT DOCUMENTS

| | | | |
|---|---|---|---|
| 7,135,030 | B2 | 11/2006 | Schwemberger et al. |
| 10,172,636 | B2 | 1/2019 | Stulen et al. |
| 10,226,274 | B2 | 3/2019 | Worrell et al. |
| 10,258,363 | B2 | 4/2019 | Worrell et al. |
| 10,335,182 | B2 | 7/2019 | Stulen et al. |
| 10,405,876 | B2 | 9/2019 | Boudreaux |
| 10,413,316 | B2 | 9/2019 | Lyons |
| 10,492,819 | B2 | 12/2019 | Hibner |
| 10,575,836 | B2 | 3/2020 | Hibner et al. |
| 10,912,581 | B2 | 2/2021 | Stulen et al. |
| 10,925,630 | B2 | 2/2021 | Cuti et al. |
| 10,987,123 | B2 | 4/2021 | Weir et al. |
| 11,337,717 | B2 | 5/2022 | Lyons |
| 2004/0002701 | A1* | 1/2004 | Ryan ....................... A61N 7/02 606/27 |
| 2006/0058825 | A1 | 3/2006 | Ogura et al. |
| 2006/0190034 | A1 | 8/2006 | Nishizawa et al. |
| 2008/0214967 | A1 | 9/2008 | Aranyi et al. |
| 2009/0163948 | A1 | 6/2009 | Sunaoshi et al. |
| 2013/0012959 | A1 | 1/2013 | Jinno |
| 2013/0140835 | A1 | 6/2013 | Stefanchik |
| 2014/0005701 | A1 | 1/2014 | Olson et al. |
| 2014/0005702 | A1 | 1/2014 | Timm et al. |
| 2014/0276931 | A1 | 9/2014 | Parihar et al. |
| 2014/0309562 | A1 | 10/2014 | Ito |
| 2014/0350570 | A1 | 11/2014 | Lee |
| 2015/0080924 | A1 | 3/2015 | Stulen et al. |
| 2016/0302812 | A1 | 10/2016 | Monroe et al. |
| 2016/0332004 | A1* | 11/2016 | Shiotani .................. B32B 9/005 |
| 2017/0143408 | A1* | 5/2017 | Worrell .......... A61B 17/320092 |
| 2018/0014846 | A1 | 1/2018 | Rhee et al. |
| 2019/0021752 | A1 | 1/2019 | Boudreaux |
| 2019/0021756 | A1 | 1/2019 | Boudreaux |
| 2019/0133635 | A1 | 5/2019 | Stulen et al. |
| 2019/0216493 | A1 | 7/2019 | Worrell et al. |
| 2019/0231385 | A1 | 8/2019 | Cowley |
| 2019/0247083 | A1 | 8/2019 | Worrell et al. |
| 2019/0290318 | A1 | 9/2019 | Boudreaux |
| 2019/0321068 | A1 | 10/2019 | Hibner et al. |
| 2019/0321069 | A1 | 10/2019 | Hibner |
| 2019/0321070 | A1 | 10/2019 | Boudreaux |
| 2019/0380735 | A1 | 12/2019 | Cuti et al. |
| 2020/0229833 | A1 | 7/2020 | Vakharia et al. |
| 2020/0229834 | A1 | 7/2020 | Olson et al. |
| 2020/0237397 | A1 | 7/2020 | Boudreaux |
| 2020/0237399 | A1 | 7/2020 | Stulen et al. |
| 2021/0059710 | A1* | 3/2021 | Black ............. A61B 17/320092 |
| 2021/0353324 | A1 | 11/2021 | Fagan et al. |
| 2021/0353325 | A1 | 11/2021 | Fagan et al. |
| 2021/0369295 | A1 | 12/2021 | Cowley |
| 2022/0249110 | A1 | 8/2022 | Lyons |

FOREIGN PATENT DOCUMENTS

| | | | |
|---|---|---|---|
| WO | 2021006984 | A1 | 1/2021 |
| WO | 2021173294 | A1 | 9/2021 |
| WO | 2021178103 | A1 | 9/2021 |
| WO | 2021202035 | A1 | 10/2021 |

OTHER PUBLICATIONS

U.S. Appl. No. 17/798,273, filed Aug. 8, 2022, Inventor: James R. Fagan.
U.S. Appl. No. 17/970,257, filed Oct. 20, 2022, Inventor: Matthew S. Cowley.
International Search Report and Written Opinion received for PCT Patent Application No. PCT/US2021/030438, mailed on Sep. 13, 2021, 17 pages.

* cited by examiner

ARTICULATING ULTRASONIC SURGICAL INSTRUMENTS AND SYSTEMS

CROSS-REFERENCE TO RELATED APPLICATION

This application is a § 371 National Stage Application of International Patent Application No. PCT/US2021/030438, filed on May 3, 2021, which claims the benefit of, and priority to, U.S. Provisional Patent Application No. 63/025,337, filed on May 15, 2020, the entire contents of each of which is hereby incorporated herein by reference.

FIELD

The present disclosure relates to surgical instruments and systems and, more particularly, to articulating ultrasonic surgical instruments and systems.

BACKGROUND

Ultrasonic surgical instruments and systems utilize ultrasonic energy, i.e., ultrasonic vibrations, to treat tissue. More specifically, a typical ultrasonic surgical instrument or system includes a transducer configured to produce mechanical vibration energy at ultrasonic frequencies that is transmitted along a waveguide to an ultrasonic end effector configured to treat, e.g., coagulate, cauterize, fuse, seal, cut, desiccate, or otherwise treat tissue.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with the present disclosure is an ultrasonic surgical instrument including a housing, an elongated shaft extending distally from the housing, an end effector extending distally from the elongated shaft, and a transducer assembly disposed at least partially within the elongated shaft. The end effector includes a jaw and an ultrasonic blade. The jaw is configured to pivot relative to the ultrasonic blade from an open position to a clamping position for clamping tissue therebetween. The transducer assembly is disposed at least partially within the elongated shaft, is distally-spaced from the housing, and includes proximal and distal transducers interconnected by a connector. The ultrasonic blade is connected to the distal transducer such that ultrasonic energy produced by the proximal transducer is transmitted along the connector and the distal transducer to the ultrasonic blade and such that ultrasonic energy produced by the distal transducer is transmitted to the ultrasonic blade.

In an aspect of the present disclosure, the connector is a flexible connector configured to articulate in at least one direction. In such aspects, the elongated shaft may include an articulating portion and the flexible connector may extend through the articulating portion such that the proximal transducer is disposed proximally of the articulating portion and such that the distal transducer is disposed distally of the articulating portion. The flexible connector may be formed as a band of material.

In another aspect of the present disclosure, the elongated shaft defines an outer diameter of less than about 15 mm, less than about 12 mm, less than about 10 mm, less than about 8 mm, less than about 5 mm, or less than about 3 mm; in aspects, between about 5 mm and about 8 mm. Alternatively or additionally, each of the proximal and distal transducers may define an outer diameter of less than 15 mm, less than about 12 mm, less than about 10 mm, less than about 8 mm, less than about 5 mm, or less than about 3 mm; in aspects, between about 5 mm and about 8 mm.

In still another aspect of the present disclosure, each of the proximal and distal transducers includes a proximal mass, a distal mass, a stack of piezoelectric elements held under pre-compression between the proximal and distal masses, and first and second electrodes electrically coupled to the stack of piezoelectric elements.

In yet another aspect of the present disclosure, the ultrasonic blade defines a cylindrical configuration. In such aspects, the jaw may be configured to rotate about the ultrasonic blade such that the jaw is capable of clamping tissue between the jaw and blade at any rotational orientation of the jaw relative to the blade.

In still yet another aspect of the present disclosure, the first and second transducers are disposed around vibration node points.

In another aspect of the present disclosure, the housing is adapted to connect to a robotic arm of a robotic surgical system. Alternatively or additionally, the housing includes at least one manual control.

In yet another aspect of the present disclosure, the proximal and distal transducers are driven by independent electrical drive signals. In such aspects, in a first mode of operation, both of the proximal and distal transducers may be activated while, in a second mode of operation, only one of the proximal or distal transducers may be activated.

In still another aspect of the present disclosure, an ultrasonic horn connects the distal transducer with the ultrasonic blade.

The details of one or more aspects of the disclosure are set forth in the accompanying drawings and the description below. Other features, objects, and advantages of the instruments and techniques described in this disclosure will be apparent from the description and drawings, and from the claims.

DETAILED DESCRIPTION

Figure 1A:
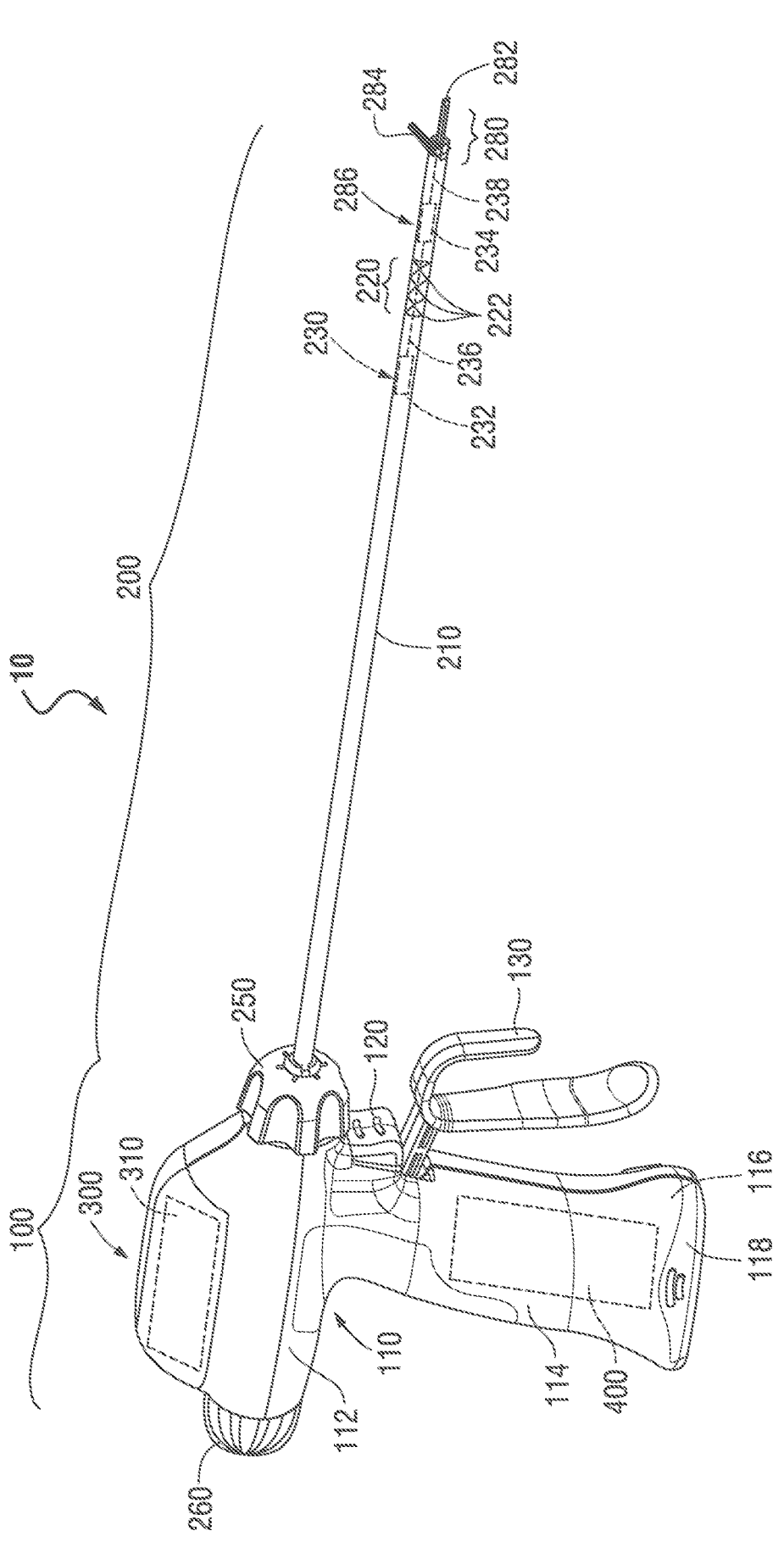
FIG. 1A is a perspective view of a hand-held articulating ultrasonic surgical instrument provided in accordance with the present disclosure, wherein the elongated assembly is disposed in an un-articulated position.
Figure 1B:
FIG. 1B is a perspective view of the hand-held articulating ultrasonic surgical instrument of FIG. 1A, wherein the elongated assembly is disposed in an articulated position.

Referring generally to FIGS. 1A and 1B, an illustrative hand-held ultrasonic surgical instrument exemplifying the aspects and features of the present disclosure is shown generally identified by reference numeral 10. For the purposes herein, hand-held ultrasonic surgical instrument 10 is generally described. Aspects and features of hand-held ultrasonic surgical instrument 10 not germane to the understanding of the present disclosure are omitted to avoid obscuring the aspects and features of the present disclosure in unnecessary detail.

Hand-held ultrasonic surgical instrument 10 generally includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support a generator assembly 300 including generator electronics 310 disposed within an outer housing. Generator assembly 300 may be permanently engaged with body portion 112 of housing 110 or removable therefrom. Alternatively, generator assembly 300 may be remotely disposed and coupled to ultrasonic surgical instrument 10 by way of a cable.

Fixed handle portion 114 of housing 110 defines a compartment 116 configured to receive a battery assembly 400 and a door 118 configured to enclose compartment 116. An electrical connection assembly (not shown) is disposed within housing 110 of handle assembly 100 and serves to electrically couple activation button 120, generator assembly 300, and battery assembly 400 with one another when generator assembly 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In configurations where generator assembly 300 is remote from ultrasonic surgical instrument 10, battery assembly 400 and the configuration of fixed handle portion 114 for receiving battery assembly 400 need not be provided, as the remote generator assembly 300 may be powered by a standard wall outlet or other remote power source.

Elongated assembly 200 of ultrasonic surgical instrument 10 includes an elongated shaft 210 having one or more articulating portions 220, a transducer assembly 230, a drive assembly (not shown), an articulation assembly (not shown), a rotation knob 250, an articulation knob 260, and an end effector 280 including a blade 282, a jaw 284, and a support shaft 286.

Elongated shaft 210 extends distally from body portion 112 of housing 110. The one or more articulating portions 220 are defined along at least a portion of elongated shaft 210. More specifically, articulating portion 220 is shown in FIGS. 1A and 1B disposed at a distal end portion of elongated shaft 210 and coupled to support shaft 286 of end effector 280 such that articulation of articulating portion 220 relative to a longitudinal axis of elongated shaft 210 articulates end effector 280 relative to the longitudinal axis of elongated shaft 210. However, it is also contemplated that additional or alternative articulating portion(s) 220 may be disposed along some or all of elongated shaft 210 periodically, intermittently, or continuously (for a portion or the entirety of elongated shaft 210). Articulating portion(s) 220 may include one or more articulation components 222, e.g., articulation joint(s), articulation linkage(s), flexible portion(s), malleable portion(s), etc., to enable articulation of end effector 280 relative to the longitudinal axis of elongated shaft 210 in at least one direction, e.g., pitch articulation and/or yaw articulation. In configurations, articulating portion(s) 220 is configured to enable both pitch articulation and yaw articulation; in other configurations, unlimited articulation in any direction is enabled.

Jaw 284 is pivotably mounted on a distal end portion of support shaft 286 and the drive assembly operably couples clamp trigger 130 of handle assembly 100 with jaw 284 of end effector 280 such that clamp trigger 130 is selectively actuatable to pivot jaw 284 relative to support shaft 286 and blade 282 of end effector 280 from a spaced-apart position to an approximated position for clamping tissue between jaw 284 and blade 282. The drive assembly may include a drive shaft, drive sleeve, drive cables, and/or other suitable components extending through handle assembly 100, elongated shaft 210 (including articulating portion 220 thereof), and support shaft 286 to operably couple clamp trigger 130 with jaw 284 and enable pivoting of jaw 284 between the spaced-apart and approximated positions regardless of the articulation of articulating portion 220. Jaw 284 includes a more-rigid structural body which is pivotably mounted on a distal end portion of support shaft 286, and a more-compliant jaw liner secured to the more-rigid structural body and positioned to oppose blade 282 to enable clamping of tissue therebetween.

Rotation knob 250 is rotatable in either direction to rotate at least a portion of elongated assembly 200 in either direction relative to handle assembly 100. More specifically, in some configurations, elongated shaft 210, transducer assembly 230, and an end effector 280 are configured to rotate together with one another relative to handle assembly 100. In other configurations, elongated shaft 210, jaw 284 of end effector 280, and support shaft 286 of end effector 280 are configured to rotate together with one another relative to handle assembly 100, transducer assembly 230, and blade 282 of end effector 280. In this configuration, jaw 284 is rotatable about blade 282 to enable orientation of jaw 284 in any suitable radial position about blade 282. Thus, jaw 284 is capable of being pivoted relative to blade 282 between the spaced-apart and approximated positions to clamp tissue between jaw 284 and blade 282 at any suitable radial position about blade 282.

The articulation assembly may include gears, pulleys, sleeves, tension cables, etc. that operably couple articulation knob 260 with the one or more articulation components 222 of articulating portion 220 such that rotation of articulation knob 260 manipulates articulating portion 220 to thereby articulate end effector 280 and support shaft 286 relative to the longitudinal axis of elongated shaft 210. Alternatively, articulation knob 260 may be operably coupled to support shaft 286 to induce the above-described articulating motion. Additional articulation actuators and/or other suitable articulation actuators (manual or powered) are also contemplated.

Figures 3, 4:
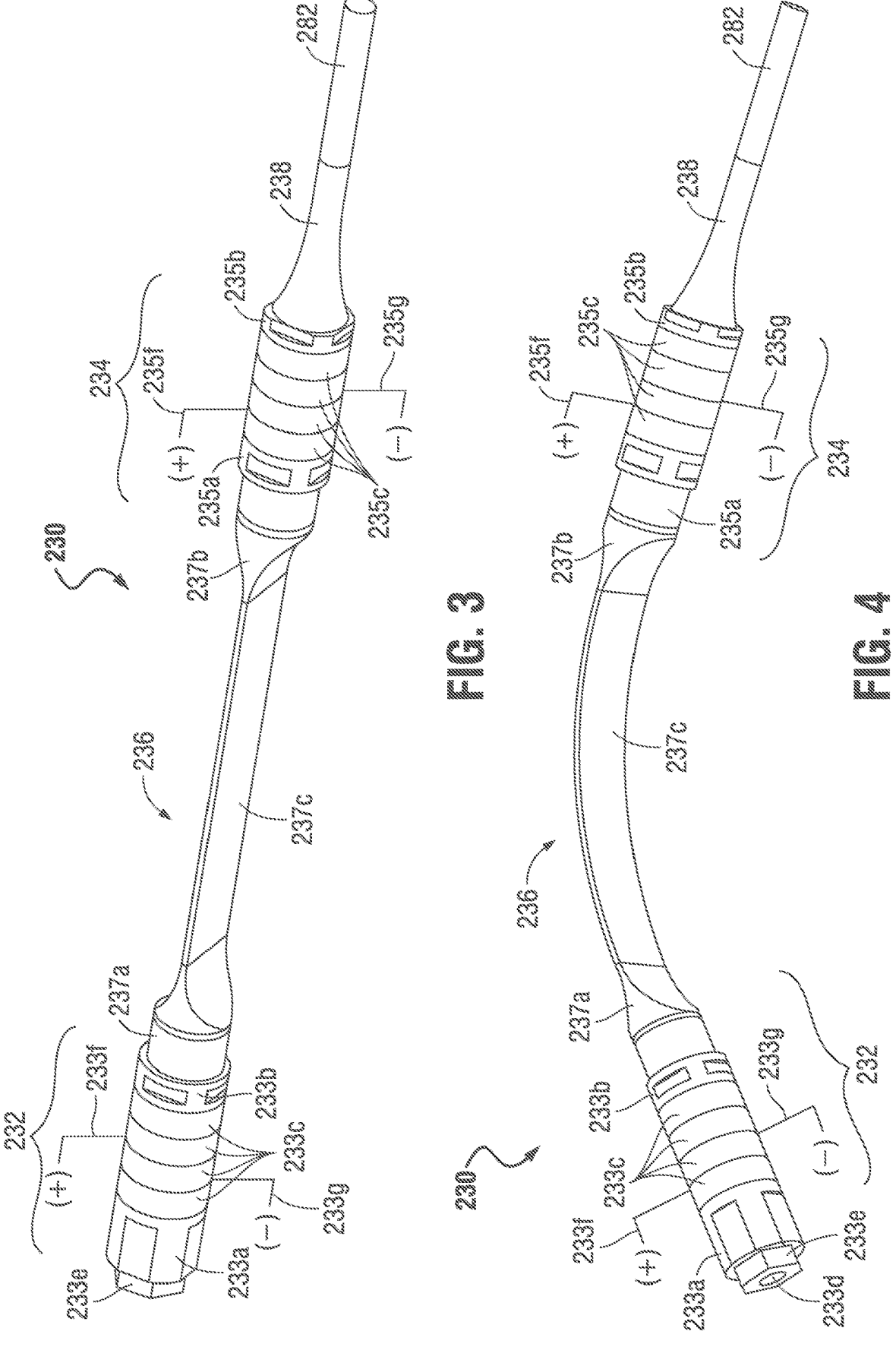
FIG. 3 is a perspective view of a transducer assembly configured for use with the articulating ultrasonic surgical instrument of FIG. 1A or any other suitable articulating ultrasonic surgical instrument, disposed in an un-articulated condition.
FIG. 4 is a perspective view of the transducer assembly of FIG. 3, disposed in an articulated condition.

With additional reference to FIGS. 3 and 4, transducer assembly 230 includes proximal and distal transducers 232, 234, respectively, a flexible connector 236 extending between proximal and distal transducers 232, 234, respectively, a distal horn 238 extending distally from distal transducer 234, and ultrasonic blade 282 which serves as the blade of end effector 280 extending distally from distal horn 238.

Transducer assembly 230 extends at least partially through elongated shaft 210, including articulating portion 220 thereof. More specifically, proximal transducer 232 is positioned proximally of an articulating portion 220 of elongated shaft 210 (e.g., the distal-most articulating portion 220 where multiple articulating portions 220 are provided), distal transducer 234 is positioned within support shaft 286 distally of the articulating portion 220 of elongated shaft 210, and flexible connector 236 extends through the articulating portion 220 of elongated shaft 210 such that, in response to articulation of articulating portion 220, flexible connector 236 is similarly articulated to thereby articulate distal transducer 234, ultrasonic horn 238, and ultrasonic blade 282 relative to proximal transducer 232. Transducer assembly 230 further extends through and distally from support shaft 286 of end effector 280 such that blade 282 is positioned to oppose jaw 284 to enable clamping of tissue therebetween. Transducer assembly 230 is described in greater detail below with reference to FIGS. 3 and 4.

It is contemplated that at least the portions of elongated shaft 210 and support shaft 286 that include transducer assembly 230 extending therethrough and, in some configurations, the entireties of elongated shaft 210 and support shaft 286, define outer diameters less than about 15 mm, less than about 12 mm, less than about 10 mm, less than about 8 mm, less than about 5 mm, less than about 3 mm, or between about 5 mm and about 8 mm, wherein "about" and similar terms as utilized herein account for material, manufacturing, use, measurement, environment, etc. tolerances; industry conventions and customs; etc., and may encompass differences of up to 10%. As such, transducer assembly 230 may define a sufficiently small diameter so as to enable operable receipt within elongated shaft 210 and support shaft 286 that is at most smaller than, for example, 15 mm, 12 mm, 10 mm, 8 mm, 5 mm, or 3 mm; transducer assembly 230 my define a diameter of between about 5 mm and about 8 mm, in some configurations. By providing a configuration with the above-noted outer diameters, ultrasonic surgical instrument 10 may be utilized minimally-invasively through access devices, e.g., trocars, having diameters of about 15 mm, about 12 mm, about 10 mm, about 8 mm, about 5 mm, or about 3 mm, respectively.

Figure 2:
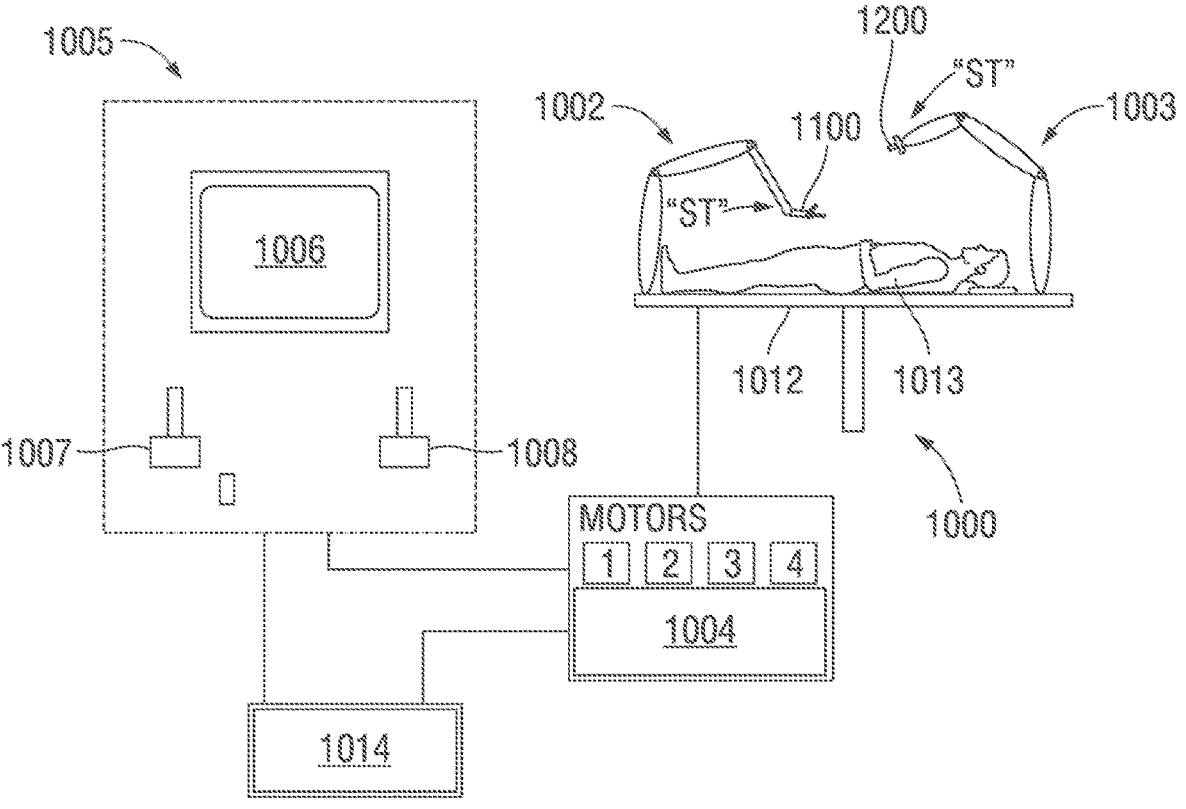
FIG. 2 is a schematic illustration of a robotic surgical system configured for use with an articulating ultrasonic surgical instrument, provided in accordance with the present disclosure.

Referring generally to FIG. 2, an illustrative robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003. Robotic surgical system 1000 may be configured for use on a patient 1013 lying on a patient table 1012 to be treated in a minimally invasive or other suitable manner.

Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, to which may be attached, for example, a surgical tool "ST" supporting an end effector assembly 1100, 1200. End effector assembly 1100 may be configured as an articulating ultrasonic surgical instrument similarly as detailed above with respect to instrument 10 (FIGS. 1A and 1B) except that housing 110 of handle assembly 100 (FIGS. 1A and 1B) is configured to connect to robot arm 1002 and any manual controls or features of instrument 10 (FIGS. 1A and 1B) are modified appropriately such that manipulation, actuation, and the other functions of instrument 10 (FIGS. 1A and 1B) are effected by robot arm 1002 rather than manually by a user. End effector 1200 may be any other suitable surgical end effector, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, and, thus, the surgical tools "ST" (including end effectors 1100, 1200) execute a desired movement and/or function according to a corresponding input from manual input devices 1007, 1008, respectively. Control device 1004 may also be configured in such a way that it regulates the movement of robot arms 1002, 1003 and/or of the motors.

Turning to FIGS. 3 and 4, transducer assembly 230 is shown in non-articulated (e.g., linear) and articulated conditions, respectively. As noted above, transducer assembly 230 includes proximal and distal transducers 232, 234, respectively, flexible connector 236 extending between proximal and distal transducers 232, 234, respectively, ultrasonic horn 238 extending distally from distal transducer 234, and ultrasonic blade 282 (which serves as the blade of end effector 280) extending distally from ultrasonic horn 238.

Proximal transducer 232 may be supported within elongated shaft 210 (FIG. 1A) in substantially fixed position relative thereto and includes a proximal end mass 233a, a distal end mass 233b, and a stack of piezoelectric elements 233c disposed between proximal and distal end masses 233a, 233b, respectively. Proximal transducer 232 further includes a stress rod 233d engaged with the distal end mass 233b, e.g., via a threaded, welded, or other suitable engagement, and extending proximally through the stack of piezoelectric elements 233c and proximal end mass 233a. A bolt 233e engaged with the stress rod 233d proximally of the proximal end mass 233a maintains the stack of piezoelectric elements 233c under a longitudinal pre-compression between proximal and distal end masses 233a, 233b, respectively, although other suitable configurations for pre-compressing the stack of piezoelectric elements 233c are also contemplated. Proximal transducer 232 additionally includes first and second electrodes 233f, 233g electrically coupled between piezoelectric elements of the stack of piezoelectric elements 233c to enable energization thereof to produce ultrasonic energy. Electrical lead wires (not shown) connect first and second electrodes 233f, 233g with generator assembly 300 (FIG. 1A) to enable an electrical drive signal generated by generator assembly 300 (FIG. 1A) to be imparted to the stack of piezoelectric elements 233c of proximal transducer assembly 232 to energize the stack of piezoelectric elements 233c to produce ultrasonic energy.

Distal transducer 234 includes a proximal end mass 235*a*, a distal end mass 235*b*, and a stack of piezoelectric elements 235*c* disposed between proximal and distal end masses 235*a*, 235*b*, respectively. A stress rod (not shown) extend between proximal end mass 235*a*, a distal end mass 235*b* and through the stack of piezoelectric elements 235*c* to maintain the stack of piezoelectric elements 235*c* under a longitudinal pre-compression between proximal and distal end masses 235*a*, 235*b*, respectively. Distal transducer 234 additionally includes first and second electrodes 235*f*, 235*g* electrically coupled between piezoelectric elements of the stack of piezoelectric elements 235*c* to enable energization thereof to produce ultrasonic energy. Electrical lead wires (not shown) connect first and second electrodes 235*f*, 235*g* with generator assembly 300 (FIG. 1A) to enable an electrical drive signal generated by generator assembly 300 (FIG. 1A) to be imparted to the stack of piezoelectric elements 235*c* of distal transducer assembly 234 to energize the stack of piezoelectric elements 235*c* to produce ultrasonic energy. The first and second electrodes 235*f*, 235*g* of distal transducer 234 may be energized via a commonly controlled and output electrical drive signal (via common or separate leads) as the first and second electrodes 233*f*, 233*g* of proximal transducer 234, respectively. Alternatively, proximal and distal transducers 232, 234, respectively, may be energized via independently controlled and output electrical drive signals from generator assembly 300 (FIG. 1A).

In some configurations, activation button 120 (FIG. 1A) itself or an additional activation button (not shown) enable activation at different levels, e.g., a first activation corresponding to a LOW power mode (producing a relatively low velocity of ultrasonic blade 282) and a HIGH power mode (producing a relatively high velocity of ultrasonic blade 282). In such configurations, only one of the transducers 232, 234 may be activated in the LOW power mode while both of the transducers 232, 234 are activated in the HIGH power moved. Alternatively, both transducers 232, 234 may be activated in both modes (with one or both of the transducers 232, 234 being activated to a different power level in the different modes).

Flexible connector 236 includes a proximal hub 237*a*, a distal hub 237*b*, and a body 237*c* extending between the proximal and distal hubs 237*a*, 237*b*, respectively. Proximal hub 237*a* is unitarily formed with or engaged to distal mass 233*b* of proximal transducer 232 while distal hub 237*b* is unitarily formed with or engaged to proximal mass 235*a* of distal transducer 234. Body 237*c* is flexible in at least one direction. In some configurations, as illustrated, body 237*c* is formed as a band of material capable of flexing in directions perpendicular to the broad side surfaces of the band of material. In other configurations, body 237*c* may include, for example, one or more reduced-dimension portions (to increase flexibility in one or more directions), flexure hinge sections, ball-and-socket joints, pinned joints, combinations thereof, and/or other suitable articulation features to enable articulation of flexible connector 236 in one or more directions.

Ultrasonic horn 238 is unitarily formed with or engaged to distal mass 235*b* of distal transducer 234 and extends distally therefrom. Blade 282 is unitarily formed with or engaged with ultrasonic horn 238 and extend distally therefrom. In some configurations, ultrasonic horn 238 is omitted and blade 282 is directly formed with or engaged to distal mass 235*b*.

Blade 282, as illustrated, defines a straight, cylindrical configuration. As detailed above, this configuration enables clamping of tissue between blade 282 and jaw 284 (FIG. 1A)

at any rotational orientation of jaw 284 (FIG. 1A) relative to blade 282 (in embodiments where jaw 284 (FIG. 1A) is rotatable about blade 282). Blade 282 may alternatively define other suitable cross-sectional configurations, e.g., polygonal configurations, and/or may include tapers along the length thereof. Further, as an alternative to defining a straight configuration, blade 282 may define a curved and/or angled configuration including one or more curved/angled portions curved/angled in similar or different directions.

Continuing with reference to FIGS. 3 and 4, as detailed above, transducer assembly 230 must define a sufficiently small diameter so as to enable operable receipt within elongated shaft 210 and support shaft 286. More specifically, proximal and distal transducers 232, 234, respectively, in some configurations, define outer diameters less than about 12 mm, less than about 10 mm, or less than about 8 mm. As a result, the diameters of the piezoelectric elements (or largest cross-sectional dimension for non-circular elements) of the stacks of piezoelectric elements 233*c*, 235*c* are limited which, in turn, limits the ultrasonic energy capable of being generated by the proximal and distal transducers 232, 234, respectively. Further, the physics of longitudinal standing waves renders the increased energy produced by increasing the number of the piezoelectric elements in the stack relatively minimal.

The above-detailed configuration of transducer assembly 230, regardless of whether transducer assembly 230 is disposed in an unarticulated condition (FIG. 3) or an articulated condition (FIG. 4), enables ultrasonic energy produced by proximal transducer 232 to be transmitted along flexible connector 236, distal transducer 234, and ultrasonic horn 238 to blade 282 and also enables ultrasonic energy produced by distal transducer 234 to be transmitted along ultrasonic horn 238 to blade 282. Thus, by providing two transducers 232, 234 producing ultrasonic energy that is transmitted to blade 282, the overall amount of ultrasonic energy provided at blade 282 can be increased without requiring an increase in the overall diameter of the system. In some devices, proximal and distal transducers 232, 234 are disposed at or near node points of the system.

Figure 5A:
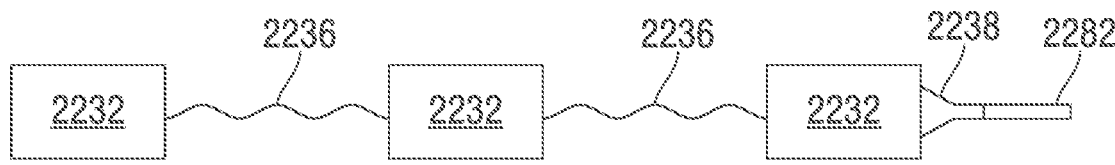
FIGS. 5A-5D are schematic illustrations of various other transducer assemblies provided in accordance with the present disclosure.

Referring to FIGS. 5A-5D, the above-detailed configuration of transducer assembly 230 (FIGS. 3 and 4) is merely exemplary; the present disclosure is not limited to two transducers connected by a flexible connector. Rather, any suitable configuration of transducers and connectors may be provided to enable a suitable amount of ultrasonic energy to be transmitted to the blade while maintaining the overall diameter of the system below a threshold diameter. For example, as illustrated in FIG. 5A, first, second, and third transducers 2232 may be provided with first and second flexible connectors 2236 disposed therebetween and an ultrasonic horn 2238 and blade 2282 extending distally from the distal-most transducer 2232.

Figure 5B:
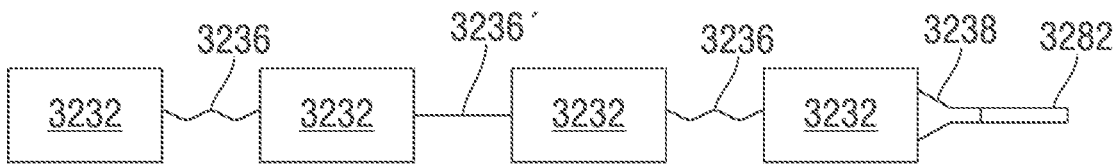

As illustrated in FIG. 5B, as another example, first, second, third, and fourth transducers 3232 may be provided with first and second flexible connectors 3236 connecting the first and second transducers 3232 and third and fourth transducers 3232, respectively, a rigid connector 3236' connecting the second and third transducers 3232 with one another, and with one another and a with one another, and an ultrasonic horn 3238 and blade 3282 extending distally from the distal-most transducer 3232.

Figure 5C:
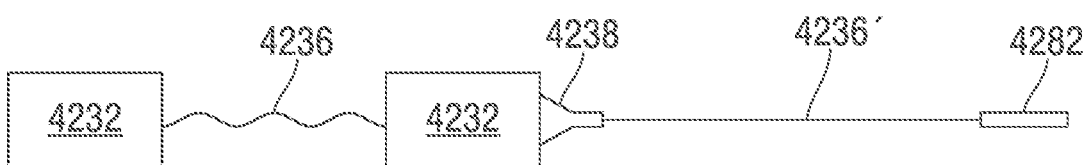

FIG. 5C illustrates still another example, wherein first and second transducers 4232 are connected by a flexible connector 4236, an ultrasonic horn 4238 extends distally from the distal-most transducer 4232, a waveguide 4236' extends distally from the ultrasonic horn 4238, and a blade 4282 is defined at or engaged to a distal end of the waveguide 4236'.

Figure 5D:
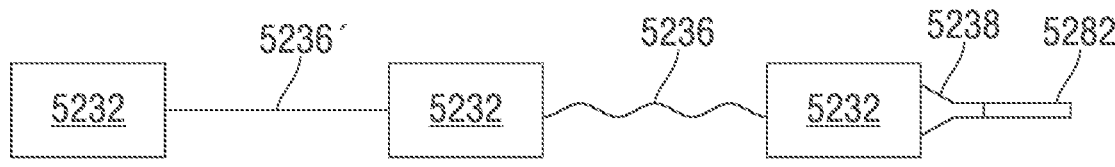

First, second, and third transducers 5232 are illustrated in FIG. 5D, wherein the first and second transducers 5232 are connected via a rigid connector 5236' and the second and third transducers 5232 are connected by a flexible connector 5236. An ultrasonic horn 5238 and blade 5282 extend distally from the distal-most transducer 5232. Other configurations including combinations of the above component or any other suitable components interconnecting multiple transducers with an ultrasonic blade are also contemplated.

The transducers, flexible connectors, ultrasonic horns, and blade of the configurations of FIGS. 5A-5D may be similar to and include any of the features of transducer assembly 230 (FIGS. 3 and 4) as detailed above. Further, the multiple flexible connectors may be oriented to allow articulation in the same plane to allow a greater degree of flexibility or in different planes to allow multidimensional articulation.

It should be understood that various aspects disclosed herein may be combined in different combinations than specifically presented in the description and accompanying drawings. Further, while several aspects of the disclosure are presented in the description and accompanying drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
a housing;
an elongated shaft extending distally from the housing, wherein the elongated shaft includes an articulating portion;
an end effector extending distally from the elongated shaft, the end effector including a jaw and an ultrasonic blade, wherein the jaw is configured to pivot relative to the ultrasonic blade from an open position to a clamping position for clamping tissue therebetween; and
a transducer assembly disposed at least partially within the elongated shaft, the transducer assembly distally-spaced from the housing and including proximal and distal transducers interconnected by a connector, wherein the connector extends through the articulating portion such that the proximal transducer is disposed proximally of the articulating portion and the distal transducer is disposed distally of the articulating portion,
wherein the ultrasonic blade is connected to the distal transducer such that ultrasonic energy produced by the proximal transducer is transmitted along the connector and the distal transducer to the ultrasonic blade and such that ultrasonic energy produced by the distal transducer is transmitted to the ultrasonic blade.

2. The ultrasonic surgical instrument according to claim 1, wherein the connector is a flexible connector configured to articulate in at least one direction.

3. The ultrasonic surgical instrument according to claim 2, wherein the flexible connector is formed as a band of material.

4. The ultrasonic surgical instrument according to claim 1, wherein the elongated shaft defines an outer diameter of less than about 15 mm.

5. The ultrasonic surgical instrument according to claim 1, wherein the elongated shaft defines an outer diameter of less than about 8 mm.

6. The ultrasonic surgical instrument according to claim 1, wherein the elongated shaft defines an outer diameter of between about 5 mm and about 8 mm.

7. The ultrasonic surgical instrument according to claim 1, wherein each of the proximal and distal transducers defines an outer diameter of less than about 15 mm.

8. The ultrasonic surgical instrument according to claim 1, wherein each of the proximal and distal transducers defines an outer diameter of less than about 8 mm.

9. The ultrasonic surgical instrument according to claim 1, wherein each of the proximal and distal transducers defines an outer diameter of between about 5 mm and about 8 mm.

10. The ultrasonic surgical instrument according to claim 1, wherein each of the proximal and distal transducers includes:
a proximal mass;
a distal mass;
a stack of piezoelectric elements held under pre-compression between the proximal and distal masses; and
first and second electrodes electrically coupled to the stack of piezoelectric elements.

11. The ultrasonic surgical instrument according to claim 1, wherein the ultrasonic blade defines a cylindrical configuration.

12. The ultrasonic surgical instrument according to claim 11, wherein the jaw is configured to rotate about the ultrasonic blade such that the jaw is capable of clamping tissue between the jaw and blade at any rotational orientation of the jaw relative to the blade.

13. The ultrasonic surgical instrument according to claim 1, wherein the proximal transducer and the distal transducer are disposed around vibration node points.

14. The ultrasonic surgical instrument according to claim 1, wherein the housing is adapted to connect to a robotic arm of a robotic surgical system.

15. The ultrasonic surgical instrument according to claim 1, wherein the housing includes at least one manual control.

16. The ultrasonic surgical instrument according to claim 1, wherein the proximal and distal transducers are driven by independent electrical drive signals.

17. The ultrasonic surgical instrument according to claim 16, wherein, in a first mode of operation, both of the proximal and distal transducers are activated and wherein, in a second mode of operation, only one of the proximal or distal transducers is activated.

18. The ultrasonic surgical instrument according to claim 1, further comprising an ultrasonic horn connecting the distal transducer with the ultrasonic blade.

* * * * *